(12) United States Patent
Inagaki

(10) Patent No.: US 8,741,118 B2
(45) Date of Patent: Jun. 3, 2014

(54) SENSOR CONTROL APPARATUS

(75) Inventor: Hiroshi Inagaki, Komaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 231 days.

(21) Appl. No.: 12/974,392

(22) Filed: Dec. 21, 2010

(65) Prior Publication Data

US 2011/0147211 A1 Jun. 23, 2011

(30) Foreign Application Priority Data

Dec. 22, 2009 (JP) ................................. 2009-291081
Nov. 22, 2010 (JP) ................................. 2010-259696

(51) Int. Cl.
*G01N 27/409* (2006.01)
*G01N 27/41* (2006.01)

(52) U.S. Cl.
USPC ........... 204/406; 204/411; 204/424; 204/425; 204/432; 73/23.31; 319/202; 319/482; 319/483; 123/680; 123/682; 123/685

(58) Field of Classification Search
USPC ................. 204/400–402, 406–412, 415–416, 204/418–419, 421–433; 205/781, 205/783.5–787; 73/23.31, 23.32; 219/201–202, 205–208, 482–506; 123/677–682, 685–686, 689
See application file for complete search history.

(56) References Cited

U.S. PATENT DOCUMENTS 2,561,441 A * 7/1951 Lou .................................. 96/112
5,895,564 A 4/1999 Miyata et al.
2004/0118202 A1* 6/2004 Iwaki et al. ................. 73/204.23
2008/0060941 A1 3/2008 Ieda et al.
2008/0277281 A1 11/2008 Hiraiwa et al.

FOREIGN PATENT DOCUMENTS

| JP | 4091347 A | 3/1992 |
|---|---|---|
| JP | 5066216 A | 3/1993 |
| JP | 5249077 A | 9/1993 |
| JP | 10104195 A | 4/1998 |
| JP | 2001295678 A | 10/2001 |
| JP | 2003-148206 A | 5/2003 |
| JP | 2006-275628 A | 10/2006 |
| JP | 2008070194 A | 3/2008 |
| JP | 2008304454 A | 12/2008 |

OTHER PUBLICATIONS

Partial English-language translation of JP 2003-148206 A.

* cited by examiner

*Primary Examiner* — Susan D Leong
(74) *Attorney, Agent, or Firm* — Sughrue Mion, PLLC

(57) ABSTRACT

A sensor control apparatus includes: a gas sensor including an oxygen concentration detection cell having a first solid electrolyte body, a reference electrode and a detection electrode, and a heater; an electric current supply unit that supplies electric current to the oxygen concentration detecting cell; an activation determination unit; a heater control unit that sets a first target temperature equal to or higher than an activation determination temperature when the activation determination unit determines that the temperature of the gas sensor is equal to or higher than the activation determination temperature; an automatic stop detection unit; and a first temperature switching unit that controls electric current supplied to the heater such that the target temperature of the heater is switched to a second target temperature different from a temperature at which blackening is generated in the first solid electrolyte body when an automatic stop is detected.

6 Claims, 5 Drawing Sheets

SENSOR CONTROL APPARATUS

BACKGROUND OF THE INVENTION

1. Field of the Invention

The present invention relates to a sensor control apparatus that calculates a concentration matching value representing a concentration of a particular gas contained in a detection target gas.

2. Description of the Related Art

In the related art, a sensor control apparatus is known that is installed in an exhaust pipe of an internal combustion engine, such as a vehicle engine, and which detects the concentration of a particular gas composition within gas flowing through an exhaust pipe. The sensor control apparatus includes, for example, a gas sensor, a heater and a control unit. The gas sensor includes a cell having a solid electrolyte body and a pair of electrodes, and outputs an electric signal corresponding to a concentration of a particular gas to the control unit. The solid electrolyte body is generally made of a zirconia-based material, particularly, partially stabilized zirconia from the viewpoint of strength and ion conductivity. In the gas sensor using such a solid electrolyte body, if the temperature of the gas sensor does not reach a predetermined temperature (e.g., 600° C. to 700° C.), the gas detection accuracy based on an electric signal corresponding to a particular gas is degraded. Therefore, when an activation determination temperature used as a reference for determining whether or not the gas sensor is activated is previously set, and a particular gas is detected, the gas sensor is heated by a heater to a temperature equal to or higher than the activation determination temperature. The control unit controls the supply of electric current for heating the heater, and calculates a concentration matching value of a particular gas based on the electric signal output from the gas sensor. In addition, also widely known are a gas sensor that includes an oxygen pump cell and an oxygen concentration detection cell using a solid electrolyte body. The oxygen concentration detection cell autonomously generates an oxygen reference against which the oxygen concentration of an exhaust gas is detected in order to control the supply of electric current to the oxygen pump cell. Also, a control unit for driving the gas sensor is also known (refer to Patent Document 1).

However, in the related art, an automatic stop control is known in which fuel consumption is improved and exhaust gas is reduced by automatically stopping the engine during a temporary stop such as a standby traffic signal. In the automatic stop control, if a condition permitting an automatic stop of the internal combustion engine is satisfied, the internal combustion engine automatically stops. If a condition permitting restart of the internal combustion engine is satisfied, the engine automatically restarts. If an electric current necessary to maintain the temperature of the gas sensor at the activation determination temperature is continuously supplied to the gas sensor during the automatic stop of the internal combustion engine, the power consumption during the automatic stop (hereinafter, also referred to as an "idling stop") of the internal combustion engine increases, and the load on the battery increases. On the other hand, for example, a control apparatus for an internal combustion engine has been proposed, in which a temperature lower than the activation determination temperature of the gas sensor is set to the target temperature of the heater during idling stop to reduce power consumption of the sensor control apparatus during the idling stop (refer to Patent Document 2).

[Patent Document 1] JP-A-2006-275628
[Patent Document 2] JP-A-2003-148206

3. Problems to be Solved by the Invention

The present inventors found that not just any heater target temperature lower than the activation determination temperature of the gas sensor may be set during the idling stop. That is, the present inventors found that the gas sensor may degrade when the heater target temperature set during the idling stop is not appropriately set. In this regard, the present inventors further discovered that the following problems occur in the type of gas sensor that includes an oxygen pump cell and an oxygen concentration detection cell using a solid electrolyte body, and where the oxygen concentration detection cell autonomously generates an oxygen reference (i.e., where oxygen is pumped from the detection electrode to the reference electrode by supplying electric current to the oxygen concentration detection cell). Specifically, the present inventors discovered that if the solid electrolyte body of the gas sensor continues to be heated to a predetermined temperature (range) lower than the activation determination temperature for a predetermined time period or longer while electric current is supplied to the oxygen concentration detection cell, the solid electrolyte body is prone to blackening. Blackening is a phenomenon where metal is generated on the surface of the solid electrolyte body in the negative electrode side when the metal oxide contained in the solid electrolyte body is chemically reduced (e.g., $ZrO_2 \rightarrow Zr + O_2$). In the gas sensor where blackening has occurred, since the ion conductivity of the solid electrolyte body decreases depending on the degree of blackening, it is difficult to detect a particular gas with high accuracy even when the gas sensor is heated to the activation determination temperature. In addition, such problems also occur in a one-cell type gas sensor that includes only an oxygen concentration detection cell, and which measures oxygen concentration depending on the electromotive force generated between a pair of electrodes of the oxygen concentration detection cell while the oxygen concentration detection cell itself autonomously generates the oxygen reference (i.e., where oxygen is pumped toward the reference electrode from the detection electrode by supplying electric current to the oxygen concentration detection cell).

SUMMARY OF THE INVENTION

The present invention has been made to address the aforementioned problems, and provides a sensor control apparatus capable of suppressing degradation of the gas sensor and reducing heater power consumption during the idling stop.

According to a first aspect, the present invention provides a sensor control apparatus comprising: a gas sensor installed in an exhaust pipe of an internal combustion engine, the gas sensor including an oxygen concentration detection cell that has a first solid electrolyte body, a reference electrode and a detection electrode, the reference electrode and the detection electrode being formed on the first solid electrolyte body and the oxygen concentration cell generating a voltage between the detection electrode and the reference electrode depending on an oxygen concentration of a measurement target gas; a heater that heats the gas sensor; an electric current supply unit that supplies an electric current to the oxygen concentration detection cell to pump oxygen from the detection electrode to the reference electrode through the first solid electrolyte body; an activation determination unit that determines whether or not a temperature of the gas sensor is equal to or higher than an activation determination temperature; and a heater control unit that controls electric current supplied to the heater by setting a first target temperature equal to or higher than the activation determination temperature as a target temperature of the heater when the activation determination unit determines that the temperature of the gas sensor is equal to or higher than the activation determination temperature, wherein the sensor control apparatus further includes: an automatic stop detection unit that detects an automatic stop of the internal combustion engine; and a first temperature switching unit that controls electric current supplied to the heater such that the target temperature of the heater is switched to a second target temperature when the automatic stop detection unit detects the automatic stop of the internal combustion engine, the second target temperature being different from a temperature at which blackening is generated in the first solid electrolyte body in a case where the electric current supply unit supplies electric current to the oxygen concentration detection cell while the temperature of the gas sensor is maintained at a temperature lower than the activation determination temperature.

In a preferred embodiment of the above first aspect, the gas sensor may include a detection chamber into which a detection target gas is introduced, and an oxygen pump cell that has a second solid electrolyte body and a pair of pump electrodes formed on the second solid electrolyte body, one electrode of which is arranged so as to be exposed to the detection chamber, and which oxygen pump cell pumps oxygen into or out of the detection chamber depending on an electric current supplied between the pair of pump electrodes, the detection electrode of the oxygen concentration detection cell being exposed to the detection chamber, and the reference electrode being positioned outside the detection chamber, and wherein the sensor control apparatus further includes an electric current supply control unit that controls electric current supplied to the oxygen pump cell depending on the voltage generated by the oxygen concentration detection cell.

If electric current is continuously supplied to the solid electrolyte body while the solid electrolyte body is heated to a predetermined temperature below the activation determination temperature, and the impedance thereof is reduced, a phenomenon may readily occur where oxygen is excessively pumped from one electrode to the other electrode, and furthermore, blackening may easily occur. Therefore, in the sensor control apparatus according to the first aspect, when automatic stop of the internal combustion engine is detected, the heater control unit controls the supply of electric current to the heater such that the temperature of the gas sensor is maintained at the aforementioned second target temperature. Therefore, the remaining time period at a temperature at which blackening is generated in the oxygen concentration detection cell (comprising the second solid electrolyte body) while electric current is supplied to the oxygen concentration detection cell does not continue for a predetermined time or longer. For this reason, in the sensor control apparatus including the gas sensor having the oxygen pump cell and the oxygen concentration detection cell, or including the gas sensor having the oxygen concentration detection cell, it is possible to suppress degradation of the gas sensor and to reduce heater power consumption during automatic stop of the internal combustion engine. Furthermore, the sensor control apparatus according to the first aspect controls electric current supply to maintain the second target temperature without stopping the supply of electric current to the heater when automatic stop of the internal combustion engine is detected. Therefore, in comparison with the case where electric current supply to the heater is cut off during automatic stop of the internal combustion engine, the sensor control apparatus can reduce the elapsed time after automatic stop of the internal combustion engine is released (automatic start) until the temperature of the gas sensor is increased to the activation determination temperature.

According to a second aspect, the present invention provides a sensor control apparatus comprising: a gas sensor for installation in an exhaust pipe of an internal combustion engine, the gas sensor including an oxygen concentration detection cell that has a first solid electrolyte body, a reference electrode and a detection electrode, the reference electrode and the detection electrode being formed on the first solid electrolyte body and the oxygen concentration cell generating a voltage between the detection electrode and the reference electrode depending on an oxygen concentration of a measurement target gas; a heater that heats the gas sensor; an electric current supply unit that supplies electric current to the oxygen concentration detection cell so as to pump oxygen from the detection electrode to the reference electrode through the first solid electrolyte body; an activation determination unit that determines whether or not a temperature of the gas sensor is equal to or higher than an activation determination temperature; and a heater control unit that controls electric current supplied to the heater by setting a first target temperature equal to or higher than the activation determination temperature as a target temperature of the heater when the activation determination unit determines that the temperature of the gas sensor is equal to or higher than the activation determination temperature, wherein the sensor control apparatus further includes: an automatic stop detection unit that detects an automatic stop of the internal combustion engine; a second temperature switching unit that controls electric current supplied to the heater such that the target temperature of the heater is switched to a third target temperature lower than the activation determination temperature of the gas sensor when the automatic stop detection unit detects an automatic stop of the internal combustion engine; and an electric current stop unit that stops supply of an electric current to the oxygen concentration detection cell when the automatic stop detection unit detects the automatic stop of the internal combustion engine.

In a preferred embodiment of the above second aspect, the gas sensor includes a detection chamber into which a detection target gas is introduced, and an oxygen pump cell that has a second solid electrolyte body and a pair of pump electrodes formed on the second solid electrolyte body, one electrode of which is arranged to be exposed to the detection chamber, and the oxygen pump cell pumps oxygen into or out of the detection chamber depending on an electric current supplied between the pair of the pump electrodes, the detection electrode of the oxygen concentration detection cell being exposed to the detection chamber, and the reference electrode being positioned outside the detection chamber, and wherein the sensor control apparatus further includes an electric current supply control unit that controls electric current supplied to the oxygen pump cell depending on the voltage generated by the oxygen concentration detection cell, and the electric current stop unit cuts off the supply of electric current to the oxygen pump cell and the oxygen concentration detection cell.

In the sensor control apparatus according to the second aspect, while the internal combustion engine automatically stops, and the electric current supply to the heater is controlled to maintain the temperature of the gas sensor at a third target temperature, the electric current supply to the oxygen concentration detection cell is cut off in the gas sensor having an oxygen concentration detection cell, and electric supply to both cells is cut off in a gas sensor having an oxygen pump cell and an oxygen concentration detection cell. For this reason, it is possible to reliably avoid blackening during the automatic stop of the internal combustion engine. Therefore, when the sensor control apparatus includes a gas sensor having an oxygen concentration detection cell, or even when the sensor control apparatus includes a gas sensor having both an oxygen concentration detection cell and an oxygen pump cell, it is possible to suppress degradation of the gas sensor and to reduce the heater power consumed during automatic stop of the internal combustion engine. Furthermore, the sensor control apparatus according to the second aspect controls the supply of electric current such that the third target temperature is maintained without cutting off electric current supply to the heater when automatic stop of the internal combustion engine is detected. For this reason, in comparison with the case where electric current supplied to the heater is cut off during automatic stop of the internal combustion engine, the sensor control apparatus can reduce the time that elapses after automatic stop of the internal combustion engine is released (automatic start) until the temperature of the gas sensor is increased to the activation determination temperature.

BRIEF DESCRIPTION OF THE DRAWINGS

Illustrative aspects of the invention will be described in detail with reference to the following figures wherein.

DETAILED DESCRIPTION OF THE PREFERRED EMBODIMENTS

Hereinafter, first to third embodiments of the sensor control apparatus of the present invention will be described with reference to the accompanying drawings. However, the present invention should not be construed as being limited thereto. In addition, in the following descriptions, the vertical direction of FIG. 2 denotes the vertical direction of the gas sensor 1, and the horizontal direction of FIG. 2 denotes the horizontal direction of the gas sensor 1.

Figure 1:
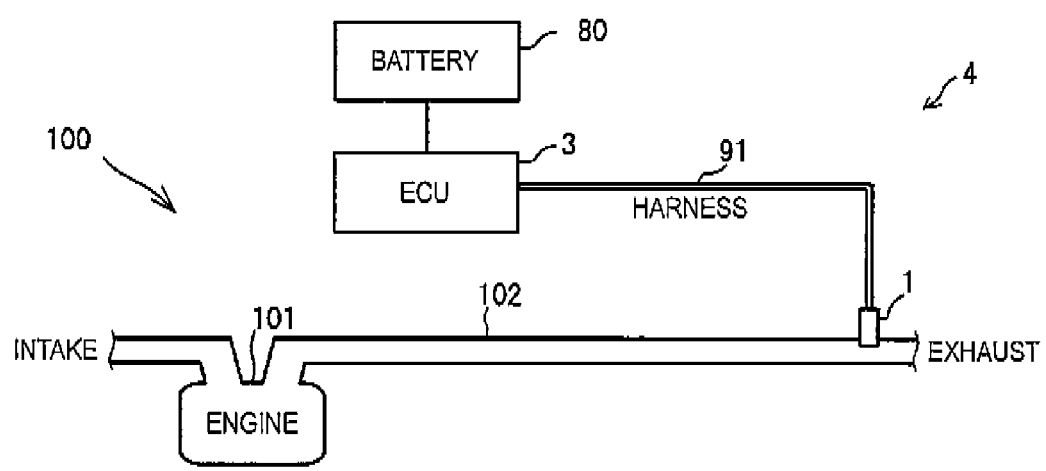
FIG. 1 is a diagram illustrating a schematic configuration around the exhaust system of the internal combustion engine 100.

The sensor control apparatus 4 according to the first to third embodiments has the same physical and electrical configurations. That is, with reference to FIG. 1, a description of the schematic configuration will be made for the internal combustion engine 100 and the sensor control apparatus 4 installed in the internal combustion engine 100. The internal combustion engine 100 has an engine 101 for driving a vehicle (not shown). The engine 101 is connected to an exhaust pipe 102 for discharging exhaust gas from the engine 101 to the external side of the vehicle. The sensor control apparatus 4 includes a gas sensor 1 and an Electronic Control Unit (ECU) 3. The gas sensor 1 is installed in the middle of the path of the exhaust pipe 102. The gas sensor 1 is a universal Air/Fuel (A/F) heated Universal Exhaust Gas Oxygen (UEGO) sensor where the gas flowing through the exhaust pipe 102 is a detection target gas. The ECU 3 is disposed in a separate position from the gas sensor 1 and driven by power received from the battery 80. The gas sensor 1 and the ECU 3 are electrically connected to each other with a harness 91 (signal line). The supply of electric power to the gas sensor 1 is controlled by the ECU 3, and the gas sensor 1 outputs an electric signal corresponding to the oxygen concentration within the detection target gas to the ECU 3. The ECU 3 executes an A/F ratio feedback control of the engine 101 based on the output from the gas sensor 1.

Figure 2:
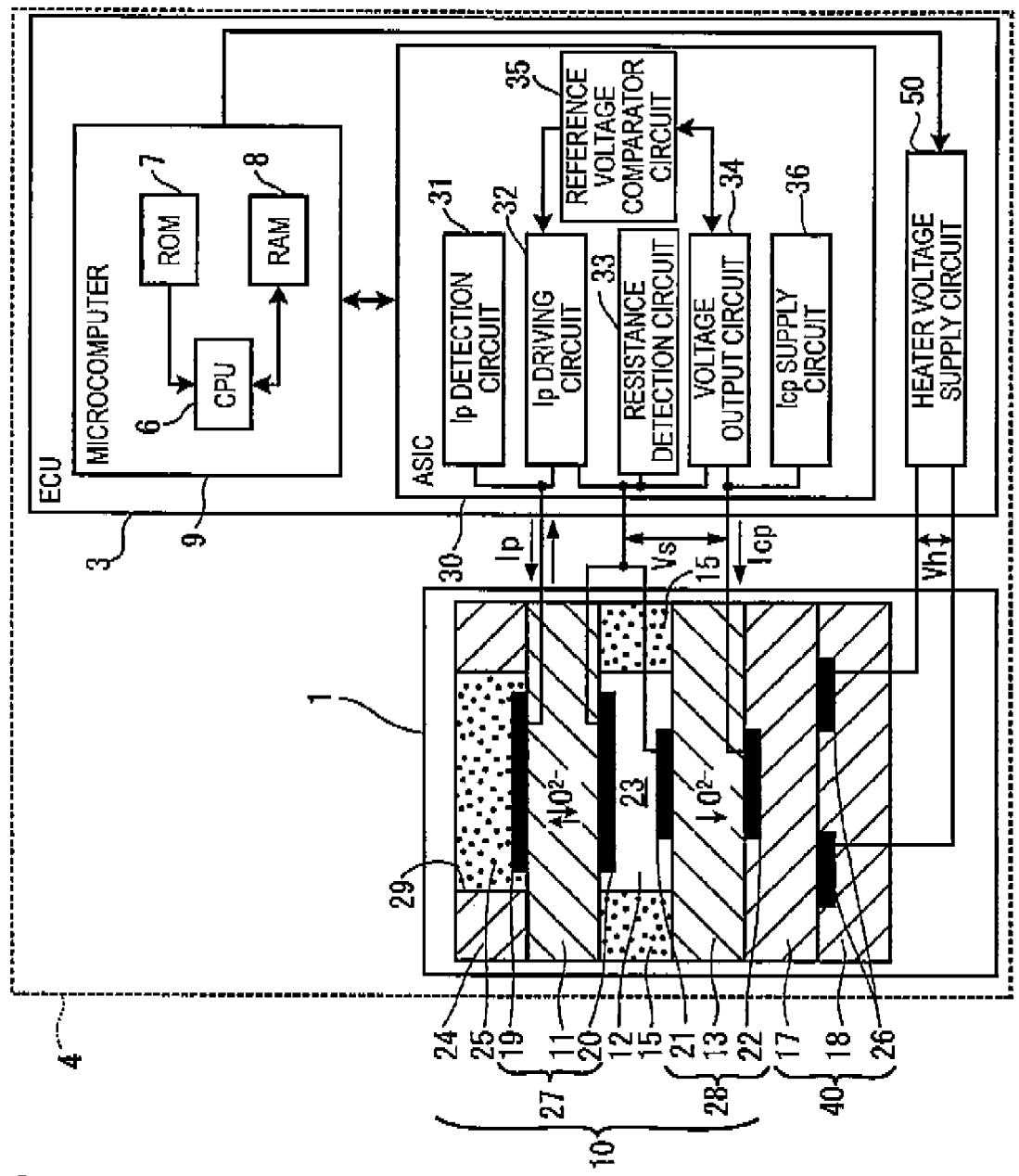
FIG. 2 is an explanatory diagram illustrating a schematic configuration of the sensor control apparatus 4.

Next, with reference to FIG. 2, the gas sensor 1 and the ECU 3 included in the sensor control apparatus 4 will be sequentially described. The gas sensor 1 includes a detection element 10, a heater element 40 and a housing (not shown). The detection element 10 has a laminated structure of the solid electrolyte bodies 11 and 13 and the insulation base bodies 12 and 24 in the order of the solid electrolyte body 13, the insulation base body 12, the solid electrolyte body 11 and the insulation base body 24. All of the solid electrolyte bodies 11 and 13, the insulation base bodies 12 and 24, and the insulation base bodies 17 and 18 described below have a long and thin plate shape. In FIG. 2, the cross-section taken along a direction perpendicular to the longitudinal direction of the gas sensor 1 is schematically illustrated. The solid electrolyte bodies 11 and 13 are made of partially stabilized zirconia as a main component containing a yttria stabilizer and have oxygen ion conductivity. The insulation base bodies 12 and 24 are made of a material containing alumina as a main component. The heater element 40 is laminated on the solid electrolyte body 13 in order to maintain activation stability of the solid electrolyte bodies 11 and 13 and early activation of the solid electrolyte bodies 11 and 13. The housing for holding the detection element 10 and the heater element 40 in the internal side is installed in the exhaust pipe 102 (refer to FIG. 1). Hereinafter, the detection element 10 and the heater element 40 included in the gas sensor 1 will be described in detail.

First, the configuration of the detection element 10 will be described with reference to FIG. 2. The detection element 10 includes a detection chamber 23, a diffusion rate control portion 15, an oxygen pump cell 27 (hereinafter, referred to as an "Ip cell 27"), an oxygen concentration detection cell 28 (hereinafter, referred to as a "Vs cell 28") and insulation base bodies 12 and 24. The detection chamber 23 is a small space into which the gas (e.g., exhaust gas) flowing through the exhaust pipe 102 (refer to FIG. 1) is introduced. The detection chamber 23 is defined by the solid electrolyte body 11, the solid electrolyte body 13, the diffusion rate control portion 15 and the insulation base body 12. The diffusion rate control portion 15 is disposed at both ends of the widthwise direction (the horizontal direction of the paper in FIG. 1) of the detection chamber 23. The diffusion rate control portion 15 is made of a porous material (e.g., alumina), and controls an inflow amount when the detection target gas is introduced into the detection chamber 23.

The Ip1 cell 27 includes a solid electrolyte body 11 and porous electrodes 19 and 20. The electrodes 19 and 20 are made of a material containing Pt as a main component. The materials containing Pt as a main component include, for example, Pt, Pt alloy, and cermet containing Pt and ceramic. The electrode 20 is provided on a surface of the solid electrolyte body 11 exposed to the detection chamber 23. The electrode 19 is provided on an surface of the solid electrolyte body 11 opposite the detection chamber 23. That is, in the laminating direction of the detection element 10, a pair of electrodes 19 and 20 are arranged so as to sandwich the solid electrolyte body 11. The insulation base body 24 is laminated on the upper surface of the solid electrolyte body 11. The insulation base body 24 has an opening 29 positioned in the upper portion of the electrode 19, and the opening 29 is provided with the protection layer 25. The protection layer 25 is formed of a porous material containing ceramic (e.g., alumina). Further, the protection layer 25 covers the upper surface of the electrode 19 so as not to be degraded by a coating component such as silicon contained in the detection target gas. The solid electrolyte body 11 corresponds to "a second solid electrolyte body" of the present invention, and the electrodes 19 and 20 correspond to "a pair of pump electrodes" of the present invention.

The Ip1 cell 27 pumps oxygen (i.e., oxygen pumping in both directions) between the atmosphere adjacent to the electrode 19 (atmosphere outside the detection element 10) and the atmosphere adjacent to the electrode 20 (atmosphere inside the detection chamber 23) by supplying an electric current between the electrodes 19 and 20.

The Vs cell 28 includes a solid electrolyte body 13 and porous electrodes 21 and 22. The solid electrolyte body 13 is disposed so as to define a bottom wall of the detection chamber 23 and face the solid electrolyte body 11. The electrode 21 is provided on a surface of the solid electrolyte body 13 that is exposed to the detection chamber 23. The electrode 22 is formed on the surface of the solid electrolyte body 13 opposite the detection chamber 23. That is, in the laminating direction of the detection element 10, a pair of electrodes 21 and 22 are disposed to sandwich the solid electrolyte body 13. The electrodes 21 and 22 are formed of a material containing the aforementioned Pt as a main component.

The Vs cell 28 mainly generates a voltage (an electromotive force) depending on an oxygen concentration difference between the atmospheres separated by the solid electrolyte body 13 (between the atmosphere adjacent to the electrode 21 inside the detection chamber 23 and the atmosphere adjacent to the electrode 22). In addition, the electrode 22 is blocked by the insulation base body 17 so as not to make contact with gas flowing through the exhaust pipe 102 (refer to FIG. 1). As described in greater detail below, the electrode 22 serves as an oxygen reference electrode for maintaining a constant oxygen concentration, and is used as a reference against which the oxygen concentration inside the detection chamber 23 is detected. The solid electrolyte body 13 corresponds to "a first solid electrolyte body" of the present invention, the electrode 21 corresponds to "a detection electrode" of the present invention, and the electrode 22 corresponds to "a reference electrode" of the present invention.

Next, the configuration of the heater element 40 will be described with reference to FIG. 2. The gas sensor 1 is activated by heating the detection element 10 (particularly, the solid electrolyte bodies 11 and 13) by means of the heater element 40. The heater element 40 includes a heat-generating resistor 26 and insulation base bodies 17 and 18. The heat-generating resistor 26 is made of a material containing platinum as a main component, and is interposed between the insulation base bodies 17 and 18. The insulation base bodies 17 and 18 are formed of a material containing alumina as a main component. The heater element 40 corresponds to "a heater" of the present invention.

Next, the configuration of the ECU 3 will be described with reference to FIG. 2. The ECU 3 controls the engine 101 of the vehicle and the gas sensor 1. Referring to FIG. 2, the ECU 3 includes as main components a microcomputer 9, an application specific integrated circuit (ASIC) 30, and a heater voltage supply circuit 50. The microcomputer 9 is a chip having the CPU 6, the ROM 7 and the RAM 8 known in the art. The ROM 7 stores various control programs executed by the CPU 6 and various parameters referenced during execution of the control programs.

As shown in FIG. 2, the ASIC 30 includes an Ip detection circuit 31, an Ip driving circuit 32, a resistance detection circuit 33, a voltage output circuit 34, a reference voltage comparator circuit 35 and an Icp supply circuit 36.

The Ip detection circuit 31 converts the electric current Ip flowing between the electrodes 19 and 20 of the Ip cell 27 into a voltage, and outputs the converted voltage to the microcomputer 9 as a detection signal. The resistance detection circuit 33 periodically supplies a predetermined electric current to the Vs cell 28, and detects a change in voltage Vs in response to the supply of the predetermined electric current. A value representing the change in voltage Vs with a change in current detected by the resistance detection circuit 33 is output to the microcomputer 9. The microcomputer 9 obtains the impedance Ri of the Vs cell 28 based on a table in which the relationship among the value output from the resistance detection circuit 33, the change amount of the voltage Vs stored in the ROM 7 and the impedance Ri of the Vs cell 28 is previously obtained. The impedance Ri of the Vs cell 28 is related to the temperature of the Vs cell 28, i.e., the temperature of the entire detection element 10, and the microcomputer 9 detects the temperature of the gas sensor 1 (detection element 10) based on the impedance Ri of the Vs cell 28.

The voltage output circuit 34 detects the electric motive force Vs generated between the electrodes 21 and 22 of the Vs cell 28. The reference voltage comparator circuit 35 compares a predetermined reference voltage and the electromotive force Vs detected by the voltage output circuit 34, and outputs the comparison result to the Ip driving circuit 32. The Ip driving circuit 32 controls the magnitude and direction of the electric current Ip supplied between the electrodes 19 and 20 of the Ip cell 27 based on the comparison result output from the reference voltage comparator circuit 35. The Icp supply circuit 36 supplies a microcurrent Icp flowing from the electrode 22 to the electrode 21 of the Vs cell 28.

The heater voltage supply circuit 50 generates a voltage Vh applied to both ends of the heat-generating resistor 26 under Proportional-Integral (PI) control in response to the instruction of the CPU 6, and the heat-generating resistor 26 heats by applying a constant voltage (e.g., 12 V) to both ends of the heat-generating resistor 26 or the like.

Next, operations for detecting the oxygen concentration of the detection target gas (the A/F ratio of the exhaust gas) using the gas sensor 1 will be described in brief with reference to FIG. 2. In addition, when the oxygen concentration of the detection target gas is detected, a reference voltage (e.g., 450 mV) is set as a comparison target of the reference voltage comparator circuit 35. First, the Icp supply circuit 36 supplies a microcurrent Icp from the electrode 22 of the Vs cell 28 to the electrode 21 through the solid electrolyte body 13. As a result of the supply of electric current, oxygen molecules within the detection target gas are converted to oxygen ions, and the oxygen ions are moved (pumped) from the electrode 21 side to the electrode 22 side through the solid electrolyte body 13. If the electric current Icp is supplied to the Vs cell 28, the oxygen ions move from the electrode 21 to the electrode 22, and an oxygen concentration atmosphere acting as a reference for generating the electromotive force Vs is generated. The voltage output circuit 34 detects the electromotive force Vs between the electrodes 21 and 22, and outputs the detected electromotive force Vs to the reference voltage comparator circuit 35. The reference voltage comparator circuit 35 compares the electromotive force Vs and the reference voltage, and outputs the comparison result to the Ip driving circuit 32. The Ip driving circuit 32 controls the magnitude and the direction of the electric current Ip supplied between the electrodes 19 and 20 of the Ip cell 27 such that the electromotive force Vs becomes the reference voltage based on the comparison result of the reference voltage comparator circuit 35. As a result, oxygen is pumped into or out of the detection chamber 23 by means of the Ip cell 27.

In addition, when the A/F ratio of the exhaust gas flowing through the detection chamber 23 is richer than a stoichiometric A/F ratio, the magnitude or the direction of the electric current Ip supplied between the electrodes 19 and 20 of the IP cell 27 is controlled to pump oxygen into the detection chamber 23 from an external side of the Ip cell 27. Meanwhile, when the A/F ratio of the exhaust gas inflowing into the detection chamber 23 is leaner than the stoichiometric A/F ratio, the magnitude and the direction of the electric current Ip supplied between the electrodes 19 and 20 of the Ip cell 27 are controlled to pump oxygen into the external side of the IP cell 27 from the detection chamber 23. The electric current Ip at this moment is converted into a voltage in the Ip detection circuit 31, and the electric current Ip converted into the voltage is output to the microcomputer 9 as a detection signal. The microcomputer 9 (CPU 6) calculates the oxygen concentration target value contained in the detection target gas and also the A/F ratio of the exhaust gas based on the detection signal.

Figure 3:
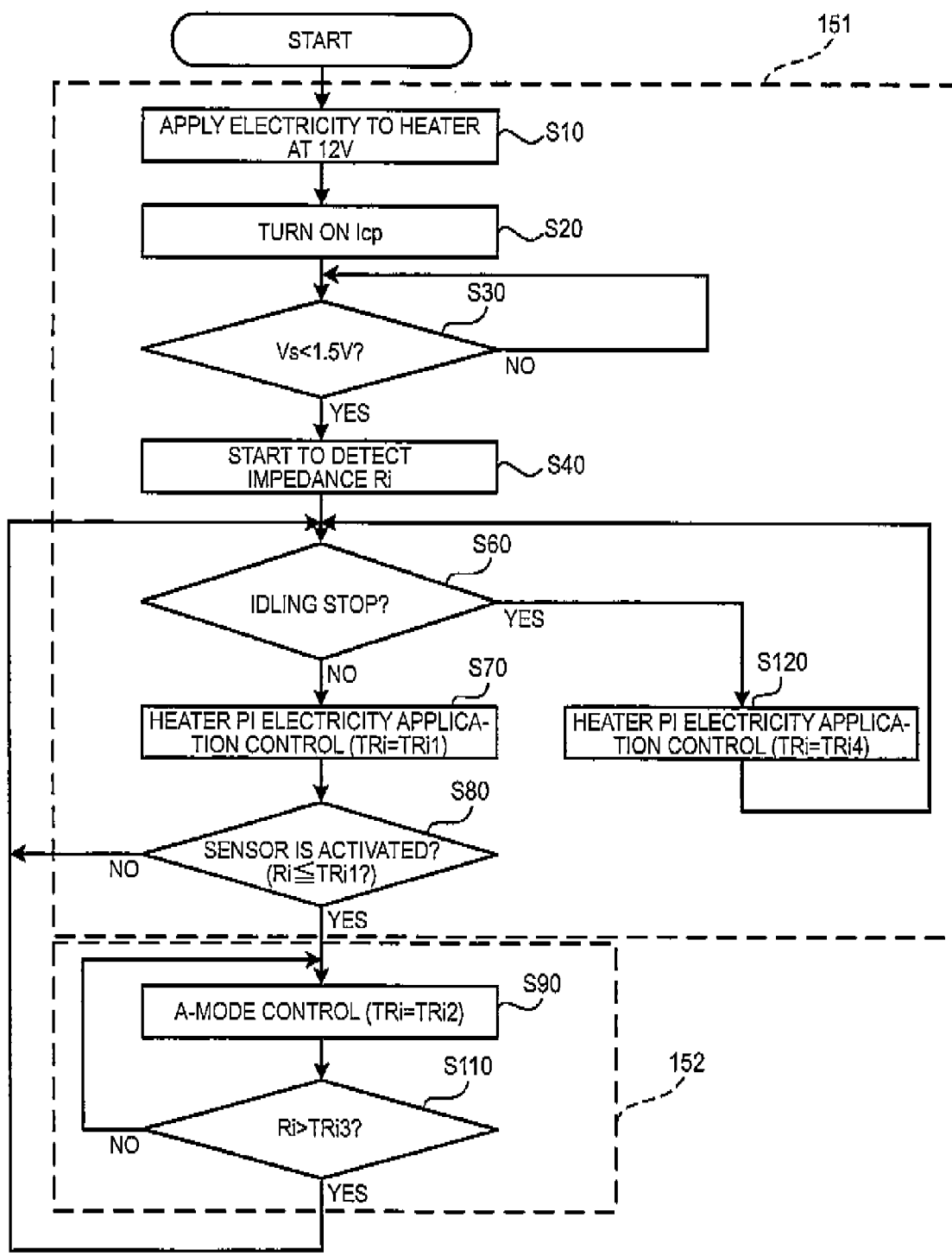
FIG. 3 is a flowchart illustrating a main process according to a first embodiment.

Next, a main process executed by the sensor control apparatus 4 according to the first embodiment will be described with reference to FIG. 3. A program for executing the main process of FIG. 3 is stored in the ROM 7 of FIG. 2 and is executed by the CPU 6. In addition, the process of calculating the oxygen concentration matching value and the A/F ratio is executed separately from the main process of FIG. 3.

First, an outline of the main process will be described. According to the first embodiment, any one of driving modes including an inactivation mode (hereinafter, referred to as an "NA-mode") and an activation mode (hereinafter, referred to as an "A-mode") is processed depending on whether or not the detection element 10 of the gas sensor 1 is activated. The NA-mode is a control mode for heating the detection element 10 to a temperature equal to or higher than the activation determination temperature. In the NA-mode, the process of supplying the electric current Ip to the Ip cell 27 is not executed. According to the first embodiment, the process represented by a box enveloped by a broken line 151 of FIG. 3 is executed in the NA-mode. The A-mode is a control mode for maintaining the temperature of the detection element 10 to be equal to or higher than the activation determination temperature, and supplying the electric current Ip for detecting the oxygen concentration within the detection target gas to the Ip cell 27. In the A-mode, the process represented by a box enveloped by a broken line 152 is executed. Furthermore, for the operating state of the internal combustion engine 100, the sensor control apparatus 4 according to the first embodiment sets the driving mode of the sensor control apparatus 4 during idling stop to the NA-mode.

According to the first embodiment, different values are set to the target resistance value corresponding to the target temperature of the heated gas sensor 1 (detection element 10) depending on the driving mode and operating state of the internal combustion engine 100. In the case where the driving mode is set to the NA-mode, and the idling stop is not carried out, the target resistance value TRi is set to a value TRi1. For the value TRi1, the resistance value in the case where the detection element 10 is activated is set. According to the first embodiment, the target resistance value TRi is used as a threshold value in the process of determining whether or not the detection element 10 is activated. In the case where the driving mode is set to the NA-mode, and the idling stop is carried out, the target resistance value TRi is set to a value TRi4. For the value TRi4, the resistance value in the case where the detection element 10 is not activated is previously set to a resistance value corresponding to a temperature where blackening is not generated in the solid electrolyte body 13.

A temperature condition for generating blackening in the solid electrolyte body 13 differs depending on conditions such as the magnitude of the electric current supplied to the solid electrolyte body 13 or the composition of the solid electrolyte body 13, and the temperature may range, for example, from 100° C. to 400° C.

When the driving mode is set to the A-mode, the target resistance value TRi is set to a value TRi2. In addition to the values TRi1 TRi2 and TRi4, according to the first embodiment, a threshold value TRi3 for detecting the case where the temperature of the detection element 10 during the A-mode control is reduced is set. For the value TRi3, a value larger than the value TRi1 is previously set. According to the first embodiment, the value TRi1 is set to 500Ω corresponding to 600° C. as the temperature of the detection element 10, the value TRi2 is set to 100Ω corresponding to 800° C. as the temperature of the detection element 10, the value TRi3 is set to 550Ω corresponding to 550° C. as the temperature of the detection element 10, and the value TRi4 is set to 580Ω corresponding to 500° C. as the temperature of the detection element 10. The value TRi4 corresponds to a temperature lower than the temperature corresponding to the threshold value TRi1 for determining whether or not the detection element 10 is activated and higher than the temperature where blackening is generated in the solid electrolyte body 13 (100° C. to 400° C.). The magnitude relationship from TRi1 to TRi4 is set to TRi4>TRi3>TRi1>TRi2.

Whether or not the internal combustion engine 100 is at an idling stop is determined, for example, based on an idling stop flag updated by an instruction of automatically stopping operation of the engine 101 and an instruction of automatically restarting operation of the engine 101 after the automatic operation stops. The idling stop flag is stored in the RAM 8. The instruction of automatically stopping operation of the engine 101 and the instruction of automatically restarting operation of the engine 101 after the automatic operation stops are output, for example, using a method known in the art (e.g., the method described in JP-A-2003-148206, incorporated herein by reference).

As shown in FIG. 3, in the main process, the CPU 6 outputs an instruction to the heater voltage supply circuit 50, and initiates a process of applying a voltage of 12V to the heat-generating resistor 26 of the heater element 40 (S10). Then, the CPU 6 outputs an instruction to the Icp supply circuit 36 in order to initiate a process of supplying electric current Icp to the Vs cell 28 (S20). Then, whether or not the voltage Vs detected by the voltage output circuit 34 is lower than 1.5 V is determined. If the voltage Vs is equal to or higher than 1.5 V (NO in step S30), the process waits until the voltage Vs becomes lower than 1.5 V. When the voltage Vs is lower than 1.5 V (YES in step S30), the CPU 6 initiates the process of detecting the impedance Ri (hereinafter, referred to as a "Ri detection process") (S40). The Ri detection process is periodically executed by the CPU 6 according to a routine separate from the main process. Specifically, in the Ri detection process, the CPU 6 outputs an instruction to the resistance detection circuit 33 to supply a constant electric current to the Vs cell 28, and outputs the change amount of the voltage Vs obtained in response to the supplied electric current to the microcomputer 9. The CPU 6 obtains the impedance Ri based on the change amount of the voltage Vs output from the resistance detection circuit 33. The Ri detection process is executed to determine whether or not the gas sensor 1 is activated based on Ri.

Then, the CPU 6 determines whether or not the idling stop is being carried out (S60). In step S60, for example, a determination is made as to whether or not the idling stop is being carried out based on the aforementioned idling stop flag. If it is determined that the idling stop is being carried out (YES in step S60), the CPU 6 initiates or continues to perform the PI electric current supply control of the heater by setting the target resistance value TRi to TRi4 (S120). Specifically, the CPU 6 outputs an instruction to the heater voltage supply circuit 50 to initiate or continue to perform the PI electric current supply control by setting the target resistance value TRi to TRi4. In addition, in the case where the electric current Ip is supplied to the Ip cell 27, the CPU 6 outputs an instruction to the Ip driving circuit 32 and the reference voltage comparator circuit 35 to stop the process of supplying the electric current Ip to the Ip cell 27 (S120). Then, the process returns to step S60.

If it is determined that the idling stop is not being carried out (NO in step S60), the CPU 6 initiates or continues to perform the PI electric supply control of the heater by setting the target resistance value TRi to TRi1 (S70). Specifically, the CPU 6 outputs an instruction to the heater voltage supply circuit 50 to initiate or continue to perform the PI electric supply control by setting the target resistance value TRi to TRi1. In addition, in the case where the electric current Ip is supplied to the Ip cell 27, the CPU 6 outputs an instruction to the Ip driving circuit 32 and the reference voltage comparator circuit 35 to stop the process of supplying the electric current Ip to the Ip cell 27 (S70). Then, the CPU 6 determines whether or not the gas sensor 1 (detection element 10) is activated (S80). According to the present embodiment, when the value Ri detected in the aforementioned Ri detection process is equal to or lower than the value Tri1, the CPU 6 determines that the gas sensor 1 is activated. When the gas sensor 1 is not activated (NO in step S80), the process returns to step S60. When the gas sensor 1 is activated (YES in step S80), the process of the A-mode (the process represented by a box enveloped by the broken line 152) is executed. Specifically, the CPU 6 initiates or continues to perform the A-mode control (S90). In step S90, the CPU 6 outputs an instruction to the Ip driving circuit 32 and the reference voltage comparator circuit 35 to initiate or continue to perform the process of supplying the electric current Ip to the Ip cell 27. In addition, the CPU 6 outputs an instruction to the heater voltage supply circuit 50 to initiate or continue to perform the PI electricity application control by setting the target resistance value TRi to TRi2.

Then, the CPU 6 determines whether or not the value Ri detected in the aforementioned Ri detection process is higher than the value TRi3 (S110). Step S110 is a process of addressing a case where the temperature of the detection element 10 decreases to a temperature at which the gas sensor 1 is determined to not be activated during the A-mode control. For example, when the automatic stop is carried out in the engine 101 (refer to FIG. 1) during the A-mode control, since the exhaust gas does not flow through the exhaust pipe 102 (refer to FIG. 1), the temperature of the gas sensor 1 is reduced. When the value Ri is equal to or lower than TRi3 (NO in step S110), the process returns to step S90. When the value Ri is higher than TRi3 (YES in step S110), the process returns to step S60. When the engine 101 automatically stops during the A-mode control, the value Ri is higher than TRi3 in step S110 (YES in step S110), and the process returns to step S60. Then, in step S60, a determination is made that the idling stop is being carried out (YES in step S60).

As described above, the CPU 6 executes the main process according to the first embodiment. Regardless of whether or not the idling stop is being carried out, the Icp supply circuit 36 and the CPU 6 that executes the process of step S20 in FIG. 3 correspond to the "electric current supply unit" of the present invention. When the driving mode is set to the NA-mode, the CPU 6 that executes the process of step S60 in FIG. 3 acts as the "automatic stop detection unit" of the present invention. When the idling stop is not being carried out (NO in step S60), the CPU 6 that executes the process of step S80 acts as the "activation determination unit" of the present invention. In addition, in step S90, the heater voltage supply circuit 50 and the CPU 6 that executes the electricity application control of the heater element 40 by setting the target resistance value TRi to TRi2 act as the "heater control unit" of the present invention. In step S90, when the driving mode is set to the A-mode (YES in step S80 and NO in step S110), the Ip driving circuit 32 and the CPU 6 that initiates or continues to perform the electric current supply control of the Ip cell 27 act as the "electric current supply control unit" of the present invention. In step S120, the heater voltage supply circuit 50 and the CPU 6 that executes the electric current supply control of the heater element 40 by switching the target resistance value TRi to TRi4 act as the "first temperature switching unit" of the present invention. In addition, the temperature corresponding to the value TRi1 corresponds to the activation determination temperature of the present invention, the temperature corresponding to the value TRi2 corresponds to the first target temperature of the present invention, and the temperature corresponding to the value TRi4 corresponds to the second target temperature of the present invention.

In the sensor control apparatus 4 according to the first embodiment, the time period at a temperature at which blackening is generated in the Vs cell 28 (solid electrolyte body 13) while the electric current Icp is supplied to the Vs cell 28 does not continue for a predetermined time or longer. Therefore, when the sensor control apparatus 4 includes the gas sensor 1 having the Vs cell 28 and the Ip cell 27, it is possible to suppress degradation of the gas sensor 1 and reduce power consumption in the heater element 40 during the automatic stop (idling stop) of the internal combustion engine 100.

In this regard, the partially stabilized zirconia as a main component of the solid electrolyte bodies 11 and 13 generally includes different phases having a plurality of crystal structures, including an M-phase (monoclinic phase), a C-phase (cubic phase), and a T-phase (tetragonal phase). It is known that the T-phase of the partially stabilized zirconia is transformed to the M-phase due to the isothermal martensite state under a predetermined condition. The transformation from the T-phase to the M-phase progresses at a highest speed when the temperature of the atmosphere to which the partially stabilized zirconia is exposed is near 200° C., and is promoted by moisture in the atmosphere to which the partially stabilized zirconia is exposed. Therefore, the temperature at which the T-phase transforms to the M-phase differs depending on conditions including the moisture in the atmosphere to which the partially stabilized zirconia is exposed and the phase structure of the partially stabilized zirconia. It is known that the transformation from the T-phase to the M-phase is accompanied by a volume change, and that when transformation from the T-phase to the M-phase occurs inside the solid electrolyte bodies 11 and 13, a crack propagates from the surface of the solid electrolyte bodies 11 and 13 to an internal side thereof so as to degrade the strength of the gas sensor 1. According to the first embodiment, the target temperature during the idling stop is set to a temperature at which blackening and transformation from the T-phase to the M-phase do not occur in the solid electrolyte bodies 11 and 13. For this reason, in the sensor control apparatus 4, since the target temperature during the idling stop is lower than the activation determination temperature of the solid electrolyte body 13, the transformation from the T-phase to the M-phase does not occur inside the solid electrolyte bodies 11 and 13. Therefore, it is possible to avoid a crack propagating from the surface of the solid electrolyte bodies 11 and 13 to the internal side thereof.

In the main process according to the first embodiment, the case where the engine 101 automatically stops during the A-mode control is detected in steps S110 and S60 executed after S110. On the other hand, in the main process according to the second embodiment, the idling stop carried out during the A-mode control may be directly detected. Hereinafter, the main process according to the second embodiment will be described with reference to FIG. 4. The program for executing the main process of FIG. 4 is stored in the ROM 7 of FIG. 2 and is executed by the CPU 6.

Figure 4:
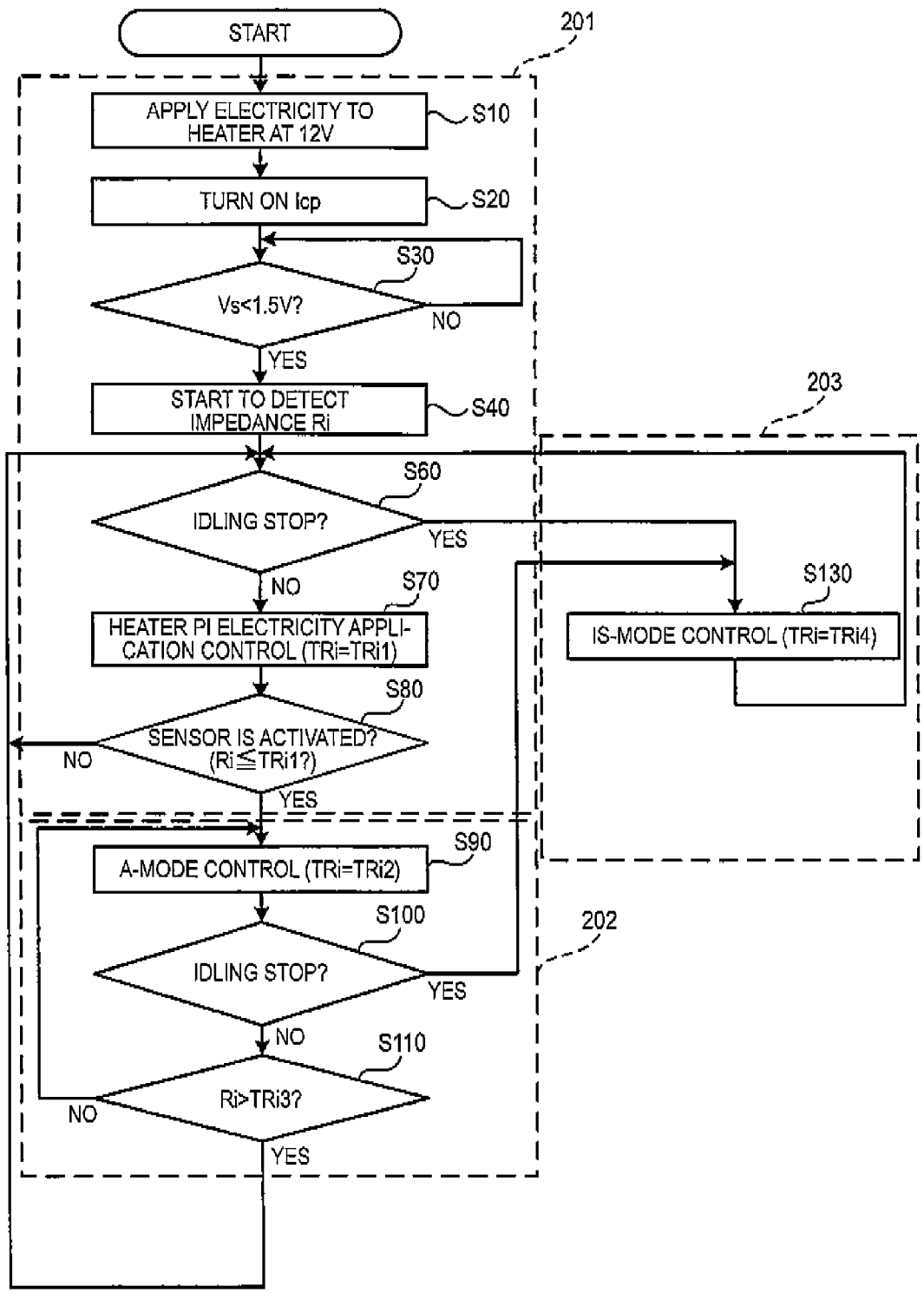
FIG. 4 is a flowchart illustrating a main process according to a second embodiment.

In FIG. 4, like step numerals denote like processes as in the main process of the first embodiment of FIG. 3. As shown in FIG. 4, in the main process according to the second embodiment, any one driving mode of the NA-mode, the A-mode, and the idling stop NA-mode (hereinafter, referred to as a "IS-mode") is processed. The IS mode is a driving mode executed during the period where the idling stop is detected. According to the second embodiment, in the NA-mode, the process represented by the box enveloped by the broken line 201 of FIG. 4 is executed. In the A-mode, the process represented by the box enveloped by the broken line 202 is executed. In the IS-mode, the process represented by the box enveloped by the broken line 203 is executed. As shown in FIG. 4, the main process according to the second embodiment is different from the main process of the first embodiment in that step S100 is executed between steps S90 and S110, and step S130 is executed instead of step S120. In step S100, similar to step S60, the CPU 6 determines whether or not the idling stop is being carried out. If it is determined that the idling stop is being carried out (YES in step S100), the process of step S130 is executed. If it is determined that the idling stop is not being carried out (NO in step S100), the process of step S110 is carried out. The process of step S130 is similar to step S120 of FIG. 3.

As described above, the CPU 6 executes the main process according to the second embodiment. The CPU 6 that executes the process of steps S60 and S100 of FIG. 4 acts as the "automatic stop detection unit" of the present invention. In the sensor control apparatus 4 according to the second embodiment, it is possible to detect the idling stop during the A-mode control at an earlier stage in comparison with the sensor control apparatus 4 of the first embodiment. Therefore, in comparison with the sensor control apparatus 4 of the first embodiment, it is possible to further reduce power consumption by the heater element 40 during the idling stop.

However, according to the first and second embodiments, blackening in the solid electrolyte body 13 during the idling stop is avoided by appropriately setting the value TRi3. On the other hand, according to the third embodiment, blackening in the solid electrolyte body 13 during the idling stop may be avoided by stopping supply of the electric current Icp during the idling stop. The main process according to the third embodiment will be described with reference to FIG. 5. The program for executing the main process of FIG. 5 is stored in the ROM 7 of FIG. 2 and is executed by the CPU 6.

Figure 5:
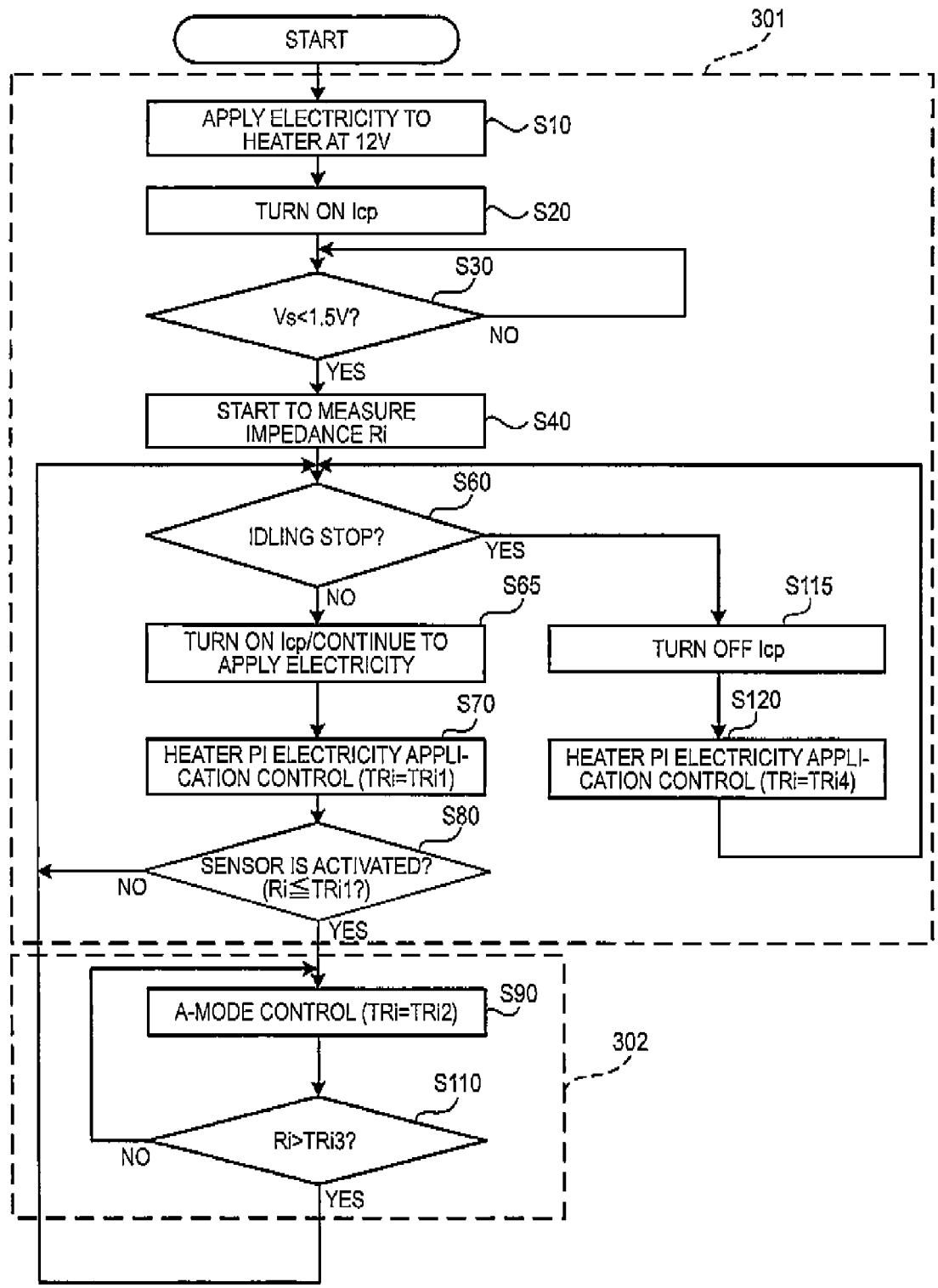
FIG. 5 is a flowchart illustrating a main process according to a third embodiment.

In FIG. 5, like step numerals denote like processes as in the main process of the first embodiment of FIG. 3. According to the third embodiment, in the NA-mode, the process represented by the box enveloped by the broken line 301 of FIG. 5 is executed. In the A-mode, the process represented by the box enveloped by the broken line 302 is executed. As shown in FIG. 5, the main process according to the third embodiment is different from the main process of the first embodiment in that steps S65 and S115 are executed.

In step S65 executed when the idling stop is not being carried out (NO in step S60), the CPU 6 outputs an instruction to the Icp supply circuit 36 to initiate or continue to supply the electric current Icp to the Vs cell 28 (S65). In step S115 executed when the idling stop is being carried out (YES in step S60), the CPU 6 outputs an instruction to the Icp supply circuit 36 to stop supplying the electric current Icp to the Vs cell 28 (S115).

As described above, the CPU 6 executes the main process according to the third embodiment. The Icp supply circuit 36 and the CPU 6 that executes the process of steps S20 and S65 of FIG. 5 according to the third embodiment correspond to the "electric current supply unit" of the present invention. The Ip driving circuit 32, the Icp supply circuit 36, and the CPU 6 that executes the process of step S115 act as the "electric current stop unit" of the present invention. The heater voltage supply circuit 50 and the CPU 6 that executes the process of step S120 act as the "second temperature switching unit" of the present invention. In addition, in FIG. 5, the temperature corresponding to the value TRi1 corresponds to the activation determination temperature of the present invention, the temperature corresponding to the value TRi2 corresponds to the first target temperature of the present invention, and the temperature corresponding to the value TRi4 corresponds to the third target temperature of the present invention.

In the sensor control apparatus 4 according to the third embodiment, during the period of carrying out the automatic stop in the internal combustion engine, supply of electric current to the Ip cell 27 and the Vs cell 28 is cut off. For this reason, it is possible to reliably avoid blackening during the automatic stop of the internal combustion engine 100 regardless of the target temperature of the gas sensor 1 during the idling stop. Therefore, even when the sensor control circuit 4 includes the gas sensor 1 comprising the Ip cell 27 and the Vs cell 28, it is possible to suppress degradation of the gas sensor 1 and to reduce power consumption by the heater element 40 during the automatic stop of the internal combustion engine 100. In addition, according to the third embodiment, since the supply of the electric current Icp to the Vs cell 28 is cut off during the idling stop, the value TRi4 is not particularly limited if it is lower than TRi1 corresponding to the activation temperature. However, the value TRi4 is preferably set to a resistance value corresponding to a temperature where the transformation from the T-phase to the M-phase does not occur in the solid electrolyte bodies 11 and 13.

In addition, the present invention is not limited to the first to third embodiments described above, but may be variously changed without departing from the spirit and scope of the claims appended hereto. For example, the following modifications (1) to (3) may be possible.

(1) While a gas sensor that detects the gas concentration of a particular composition within the detection target gas is exemplified as a universal A/F heated exhaust gas oxygen (UEGO) sensor in the aforementioned embodiments, the present invention is not limited thereto. For example, in addition to the oxygen pump cell and the oxygen concentration detection cell described above, a second oxygen pump cell in which oxygen is pumped out by decomposing NOx may be further included. The present invention may be applied to an NOx sensor that detects the concentration of NOx within the detection target gas.

In addition, the present invention is not limited to a two-cell type gas sensor having an oxygen pump cell (Ip cell) and an oxygen concentration detection cell (Vs cell), and may be applied to a one-cell type gas sensor having an oxygen concentration detection cell (Vs cell) 28, in which, similar to the aforementioned embodiment, oxygen is pumped toward the electrode 21 from the electrode 22 by supplying a microcurrent Icp to the electrode (reference electrode) 21 from the electrode (detection electrode) 22 in the Vs cell 28. In such a one-cell type gas sensor, the oxygen concentration within the detection target gas is detected depending on the voltage (electromotive force) generated between a pair of the electrodes 21 and 22 of the Vs cell 28, and the sensor control apparatus connected to this gas sensor determines whether the A/F ratio of the exhaust gas is rich or lean in comparison with a particular A/F ratio based on the voltage generated between a pair of the electrodes 21 and 22.

Even in the one-cell type gas sensor having such a Vs cell 28, the electrode (reference electrode) 21 is used as a reference oxygen source by supplying the microcurrent Icp. Therefore, by connecting the gas sensor to the sensor control apparatus according to the first to third embodiments described above, it is possible to reduce the power consumption in the heater element 40 during the automatic stop (idling stop) of the internal combustion engine 100 while degradation of the gas sensor the Vs cell 28) is suppressed. In addition, in the case where the sensor control apparatus 4 according to the first to third embodiments is connected to a gas sensor having a single Vs cell 28, a basically similar configuration may be adopted differing in that a circuit system for driving the oxygen pump cell is omitted, and a process relating to the oxygen pump cell is omitted from the flowchart of each embodiment.

(2) The configuration of the sensor control apparatus 4 may be appropriately modified. For example, the control unit having the microcomputer 9, the ASIC 30, and the heater voltage supply circuit 50, and the ECU 3 may be separately provided. In this case, the main process described above may be executed in the control unit or the ECU 3. In addition, for example, while the sensor control apparatus 4 of the aforementioned embodiments controls electric current supply to the heater element 40 using the target resistance value TRi including TRi1, TRi2 and TRi4 through the PI electric current supply control, a method of controlling electric current supply to the heater element 40 is not limited thereto, but may be performed through a PID electric current supply control.

(3) The steps executed in the main process and various parameters referenced in the main process described above may be appropriately modified. For example, while the temperature of the detection element 10 is detected based on the impedance of the Vs cell 28 in the aforementioned embodiments, the temperature of the detection element 10 may be detected based on the impedance of the Ip cell 27 instead of the Vs cell 28. In addition, the temperature of the detection element 10 may be detected based on the resistance value of the heat-generating resistor 26 included in the heater element 40. In addition, for example, the sensor control apparatus 4 according to the first and second embodiments cuts off electric current supply to the Ip cell 27 during the idling stop from the viewpoint of reducing power consumption. However, the sensor control apparatus 4 according to the first and second embodiments may continue to supply electric current to the Ip cell 27 during the idling stop if the target temperature of the heater element 40 during the idling stop is a temperature at which blackening is not generated in both the solid electrolyte body 11 and the solid electrolyte body 13. In addition, for example, according to the third embodiment, a determination as to whether the idling stop is being carried out may be made during the A-mode control as in step S100 of the second embodiment of FIG. 4.

This application claims priority from Japanese Patent Application No. 2009-291081, which was filed on Dec. 22, 2009, and from Japanese Patent Application No. 2010-259696, which was filed on Nov. 22, 2010, the disclosures of which are herein incorporated by reference in their entirety.

What is claimed is:

1. A sensor control apparatus comprising:
a gas sensor for installation in an exhaust pipe of an internal combustion engine,
the gas sensor including an oxygen concentration detection cell comprising a first solid electrolyte body, a reference electrode and a detection electrode, the reference electrode and the detection electrode being formed on the first solid electrolyte body and the oxygen concentration cell generating a voltage between the detection electrode and the reference electrode depending on an oxygen concentration of a measurement target gas;
a heater that heats the gas sensor;
an electric current supply unit that supplies electric current to the oxygen concentration detection cell so as to pump oxygen from the detection electrode to the reference electrode through the first solid electrolyte body;
an activation determination unit that determines whether or not a temperature of the gas sensor is equal to or higher than an activation determination temperature; and
a heater control unit programmed to control electric current supplied to the heater by setting a first target temperature equal to or higher than the activation determination temperature as a target temperature of the heater when the activation determination unit determines that the temperature of the gas sensor is equal to or higher than the activation determination temperature,
wherein the sensor control apparatus further includes:
an automatic stop detection unit that detects an automatic stop of an internal combustion engine; and
a first temperature switching unit programmed to control electric current supplied to the heater such that the target temperature of the heater is switched to a second target temperature when the automatic stop detection unit detects the automatic stop of the internal combustion engine, the second target temperature being different from a temperature at which blackening is generated in the first solid electrolyte body in a case where the electric current supply unit supplies electric current to the oxygen concentration detection cell while the temperature of the gas sensor is maintained at a temperature lower than the activation determination temperature,
wherein the heater control unit is programmed to control electric current supplied to the heater by switching a target resistance value to a first target resistance value corresponding to the first target temperature when the activation determination unit determines that the temperature of the gas sensor is equal to or higher than the activation determination temperature, and
wherein the first temperature switching unit is programmed to control electric current supplied to the heater by switching the target resistance value to a second target resistance value corresponding to the second target temperature when the automatic stop detection unit detects the automatic stop of the internal combustion engine.

2. The sensor control apparatus according to claim 1,
wherein the gas sensor includes
a detection chamber into which the detection target gas is introduced, and
an oxygen pump cell that has a second solid electrolyte body and a pair of pump electrodes formed on the second solid electrolyte body, one of which is arranged so as to be exposed to the detection chamber, the oxygen pump cell pumping oxygen into or out of the detection chamber depending on an electric current supplied between the pair of pump electrodes, the detection electrode of the oxygen concentration detection cell being exposed to the detection chamber, and the reference electrode being positioned outside the detection chamber, and wherein the sensor control apparatus further includes an electric current supply control unit that controls electric current supplied to the oxygen pump cell depending on the voltage generated by the oxygen concentration detection cell.

3. A sensor control apparatus comprising:

a gas sensor for installation in an exhaust pipe of an internal combustion engine, the gas sensor including an oxygen concentration detection cell comprising a first solid electrolyte body, a reference electrode and a detection electrode, the reference electrode and the detection electrode being formed on the first solid electrolyte body and the oxygen concentration cell generating a voltage between the detection electrode and the reference electrode depending on an oxygen concentration of a measurement target gas;

a heater that heats the gas sensor;

an electric current supply unit that supplies electric current to the oxygen concentration detection cell so as to pump oxygen from the detection electrode to the reference electrode through the first solid electrolyte body;

an activation determination unit that determines whether or not a temperature of the gas sensor is equal to or higher than an activation determination temperature; and a heater control unit programmed to control electric current supplied to the heater by setting a first target temperature equal to or higher than the activation determination temperature as a target temperature of the heater when the activation determination unit determines that the temperature of the gas sensor is equal to or higher than the activation determination temperature, wherein the sensor control apparatus further includes:

an automatic stop detection unit that detects an automatic stop of an internal combustion engine;

a second temperature switching unit programmed to control electric current supplied to the heater such that the target temperature of the heater is switched to a third target temperature lower than the activation determination temperature of the gas sensor when the automatic stop detection unit detects an automatic stop of the internal combustion engine; and an electric current stop unit programmed to stop supply of electric current to the oxygen concentration detection cell when the automatic stop detection unit detects the automatic stop of the internal combustion engine, wherein the heater control unit is programmed to control electric current supplied to the heater by switching a target resistance value to a first target resistance value corresponding to the first target temperature when the activation determination unit determines that the temperature of the gas sensor is equal to or higher than the activation determination temperature, and wherein the second temperature switching unit is programmed to control electric current supplied to the heater by switching the target resistance value to a third target resistance value corresponding to the third target temperature when the automatic stop detection unit detects the automatic stop of the internal combustion engine.

4. The sensor control apparatus according to claim 3, wherein the gas sensor includes a detection chamber into which a detection target gas is introduced, and an oxygen pump cell that has a second solid electrolyte body and a pair of pump electrodes formed on the second solid electrolyte body, one of which is arranged so as to be exposed to the detection chamber, the oxygen pump cell pumping oxygen into or out of the detection chamber depending on an electric current supplied between the pair of pump electrodes, the detection electrode of the oxygen concentration detection cell being exposed to the detection chamber, and the reference electrode being positioned outside the detection chamber, and wherein the sensor control apparatus further includes an electric current supply control unit that controls electric current supplied to the oxygen pump cell depending on the voltage generated in the oxygen concentration detection cell, and the electric current stop unit stops supply of the electric current to the oxygen pump cell and the oxygen concentration detection cell.

5. The sensor control apparatus according to claim 1, wherein the second target temperature is greater than 400° C.

6. The sensor control apparatus according to claim 1, wherein the second target temperature is approximately 500° C.

* * * * *